United States Patent [19]

Rew et al.

[11] Patent Number: 5,514,643
[45] Date of Patent: May 7, 1996

[54] 2-AMINOTHIAZOLECARBOXAMIDE DERIVATIVES, PROCESSES FOR PREPARING THE SAME AND USE THEREOF FOR CONTROLLING PHYTOPATHOGENIC ORGANISMS

[75] Inventors: Yo S. Rew; Jinho Cho; Choon S. Ra; Sei-chang Ahn; Sung K. Kim; Yong-Hwan Lee; Bon Y. Jung; Woo B. Choi; Young H. Rhee; Man Y. Yoon; Sung W. Chun, all of Daejeon, Rep. of Korea

[73] Assignee: Lucky Ltd., Rep. of Korea

[21] Appl. No.: 287,917

[22] Filed: Aug. 9, 1994

[30] Foreign Application Priority Data

Aug. 16, 1993 [KR] Rep. of Korea .................. 93-15846

[51] Int. Cl.$^6$ .................. A01N 43/78; C07D 277/40; C07D 277/42; C07D 277/44
[52] U.S. Cl. .................. 504/266; 548/194; 549/59; 549/473; 504/289; 504/294
[58] Field of Search .................. 548/194; 514/370; 504/266

[56] References Cited

U.S. PATENT DOCUMENTS

5,039,694  8/1991  Suzuki et al. .................. 514/406
5,264,448  11/1993  Shuto et al. .................. 514/324

FOREIGN PATENT DOCUMENTS

0538231  4/1993  European Pat. Off. .

OTHER PUBLICATIONS

Chemical Abstracts, vol. 115:280019f, (1991).
Chemical Abstracts, vol. 120:156698r, (1994).

*Primary Examiner*—Johann Richter
*Assistant Examiner*—Laura R. Cross
*Attorney, Agent, or Firm*—Birch, Stewart, Kolasch & Birch

[57] ABSTRACT

The present invention relates to a novel 2-aminothiazole-carboxamide derivative represented by the following general formula (I):

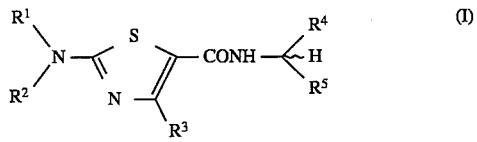

in which $R^1$-$R^5$ are defined herein, which is a fungicidal agent useful for controlling phytopathogenic organisms. In addition, the present invention also relates to a process for preparing the novel 2-aminothiazolecarboxamide derivative of formula (I) and use of the compound of formula (I) as an agent for controlling phytopathogenic organisms.

14 Claims, No Drawings

2-AMINOTHIAZOLECARBOXAMIDE DERIVATIVES, PROCESSES FOR PREPARING THE SAME AND USE THEREOF FOR CONTROLLING PHYTOPATHOGENIC ORGANISMS

BACKGROUND OR THE INVENTION

1. Field of the invention

The present invention relates to a novel thiazolecarboxamide derivative. More particularly, the present invention relates to a novel 2-aminothiazolecarboxamide derivative represented by the following general formula (I):

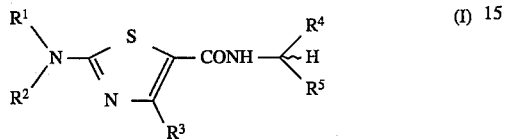

in which
$R^1$ and $R^2$ independently of one another represent hydrogen, $(C_1-C_5)$alkyl, $(C_1-C_5)$haloalkyl, $(C_3-C_6)$alkenyl, $(C_3-C_6)$alkynyl, $(C_3-C_6)$cycloalkyl,

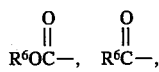

or phenyl or benzyl, each of which can be substituted with halogen, $(C_1-C_3)$ alkyl or nitro;
$R^3$ represents $(C_1-C_3)$alkyl or $(C_1-C_3)$haloalkyl;
$R^4$ represents 2-thienyl, 3-thienyl, 2-furyl, 3-furyl, phenyl, or benzyl, each of which can be substituted with halogen, $(C_1-C_6)$alkyl or nitro;
$R^5$ represents cyano or thiocarbamoyl; and
$R^6$ represents $(C_1-C_6)$alkyl, $(C_3-C_6)$alkenyl, $(C_3-C_6)$cycloalkyl, or phenyl or benzyl, each of which can be substituted with halogen, $(C_1-C_3)$alkyl or nitro.

The present invention also relates to a process for preparing the compound of formula (I), as defined above, and use of the compound of formula (I) for controlling phytopathogenic organisms.

2. Background Art

Fungicidal agents against Oomycetes occupy approximately 25% of the total fungicide market and have built up a unique market because Oomycetes is characterized by mycelium having no ergosterol biosynthesis mechanism. At the present time, conventional non-systemic fungicidal agents, for example, captan, captafol, dithiocarbamate, chlorothalonil, etc., have been widely used for controlling Oomycetes. However, it has been disclosed that such non-systemic fungicidal agents have only a preventive activity against Oomycetes but have serious toxic effect. In the 1970's acylalanine-based fungicidal agents were developed as a systemic fungicide. However, it has been also reported that the resistance of Oomycetes to such systemic fungicides becomes gradually aggravated. Further, recently the field of fungicidal agents against Oomycetes has not achieved any remarkable development. Accordingly, the development of a novel fungicide against Oomycetes which has a high fungicidal activity and a low toxicity has been strongly desired.

To satisfy such a requirement, in the latter half of the 1980's dimethomorph was developed and reported as an agent for controlling causative organisms of late blight and downy mildew in fruit trees and potatoes. In addition, for disinfecting cereal seeds and controlling causative organisms of rust and smut metsulfovax represented by the following formula (II) was developed (see S. African Patent No. 67 06,681):

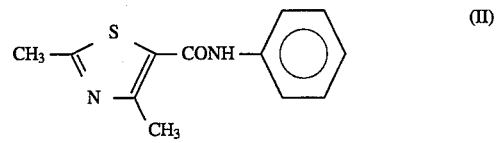

Thereafter, the following thiazolecarboxamide-based compounds have also been proposed as an effective substance having fungicidal activity against Oomycetes:
1) Heterocyclic carboxamide compounds represented by the following general formula (see European Patent No. 268, 892):

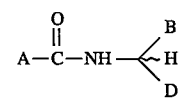

in which
A denotes pyrazolyl, imidazolyl, thiazolyl, isothiazolyl, oxazolyl or isoxazolyl, each of which has substituent(s),
B denotes alkoxy, alkylthio, imidazolyl, pyrazolyl, furyl or thienyl, and
D denotes cyano, thiocarbamoyl or acylthiocarbamoyl.

Among the above-identified heterocyclic carboxamide compounds, the compound having the following formula (III) has been proposed as a typical effective substance:

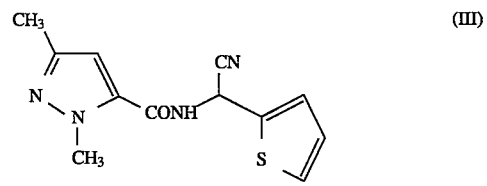

and has been reported as having a significant preventive and curative effects on Pseudoperonospora cubensis, which is the causative organism of downey mildew in cucumber, at a concentration of 100 ppm.
2) Thiazolecarboxamide compounds represented by the following general formula (see European Patent No. 292,937 and Japanese Laid-open Patent Publication No. (Hei) 4-154704 (1992)):

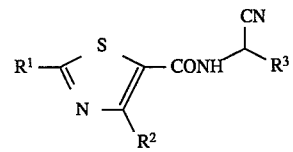

in which
$R^1$ and $R^2$ represent hydrogen or $(C_1-C_3)$alkyl, and
$R^3$ represents 2-furyl, 3-furyl, 2-thienyl or 3-thienyl.

Among the above-identified thiazolecarboxamide compounds, the compound having the following formula (IV) has been proposed as a typical effective substance:

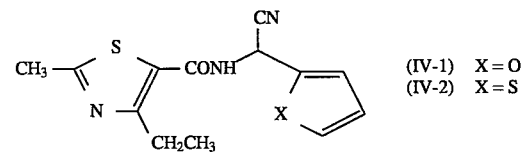

(IV-1) X = O
(IV-2) X = S and it has been reported that the compounds (IV-1) and (IV-2) prevent tomato late blight by 70% and 80%, respectively at a concentration of 25 ppm.

3) Thiazolecarboxamide compounds represented by the following general formula (see European Patent No. 313,091):

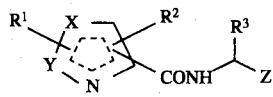

in which
one of X and Y represents S and the other represents C,
Z represents cyano or thiocarbamoyl,
$R^1$ and $R^2$ independently of one another represent hydrogen, halogen, $(C_1-C_6)$alkyl, halomethyl or phenyl, and
$R^3$ represents $(C_2-C_6)$alkenyl, $(C_2-C_4)$haloalkenyl, furyl, thienyl, $(C_1-C_4)$alkoxy, $(C_1-C_4)$alkylthio, $(C_3-C_5)$alkynyloxy, $(C_3-C_5)$alkynylthio, pyrazolyl, or phenyl which can be substituted with halogen.

4) Thiazolecarboxamide compounds represented by the following general formula (see European Patent No. 434,620):

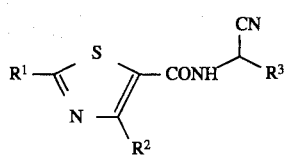

in which
$R^1$ and $R^2$ independently of one another represent hydrogen, alkyl, cycloalkyl (which can be substituted with methyl or methylthio) or —$CH_2XR^4$,
$R^3$ represents furyl or thienyl,
$R^4$ represents alkyl, alkenyl or alkynyl (each of which can be substituted with halogen or alkoxy), or phenyl or benzyl (each of which can be substituted with halogen, alkyl, alkoxy, trifluoromethyl or nitro), and
X represents oxygen or sulfur atom.

As the typical effective substance of the above-identified compounds, the compound having the following formula (V):

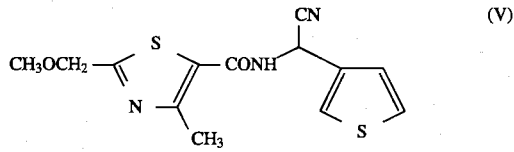

was proposed and it has been reported that the compound of formula (V) controls tomato late blight by 90% or more at a concentration of 60 ppm.

The above exemplified, effective thiazole carboxamide compounds have a certain degree of fungicidal activity and also a low toxicity. However, they have a disadvantage in that their fungicidal activities are lower than that of dimethomorph which was developed and commercialized in the latter half of the 1980's.

Thus, the present inventors have extensively studied to develop a new compound having a high fungicidal activity and a low toxicity. As a result, we have identified that a certain thiazolecarboxamide derivative having an amino group attached to the 2-position of the thiazole ring, i.e. a novel 2-aminothiazolecarboxamide derivative having the general formula (I), as defined above, shows a potent fungicidal activity which is higher than those of the presently known thiazolecarboxamide compounds and dimethomorph, and also has a systemic activity and a curative activity as well as a preventive activity, and then completed the present invention.

Therefore, it is an object of the present invention to provide a novel 2-aminothiazolecarboxamide derivative having the general formula (I), as defined above.

It is a further object of the present invention to provide a process for preparing the 2-aminothiazolecarboxamide derivative of formula (I).

It is another object of the present invention to provide a use of the 2-aminothiazolecarboxamide derivative of formula (I) as an agent for controlling plant diseases caused by typical phytopathogenic organisms of Oomycetes.

The more pertinent and important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purpose of the present invention. Further, those skilled in the art can realize that such equivalent constructions do not depart from the spirit and scope of the invention as set forth in the claims.

DISCLOSURE OF INVENTION

In one aspect, the present invention relates to a novel 2-aminothiazolecarboxamide derivative represented by the following general formula (I):

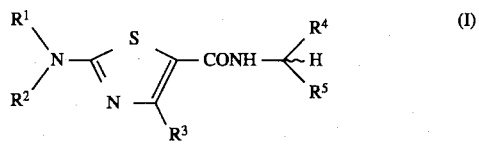

in which
$R^1$ and $R^2$ independently of one another represent hydrogen, $(C_1-C_5)$alkyl, $(C_1-C_5)$haloalkyl, $(C_3-C_6)$alkenyl, $(C_3-C_6)$alkynyl, $(C_3-C_6)$cycloalkyl,

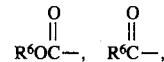

or phenyl or benzyl, each of which can be substituted with halogen, $(C_1-C_3)$alkyl or nitro;
$R^3$ represents $(C_1-C_3)$alkyl or $(C_1-C_3)$haloalkyl;
$R^4$ represents 2-thienyl, 3-thienyl, 2-furyl, 3-furyl, phenyl, or benzyl, each of which can be substituted with halogen, $(C_1-C_6)$alkyl or nitro;
$R^5$ represents cyano or thiocarbamoyl; and
$R^6$ represents $(C_1-C_6)$alkyl, $(C_3-C_6)$alkenyl, $(C_3-C_6)$cycloalkyl, or phenyl or benzyl, each of which can be substituted with halogen, $(C_1-C_3)$alkyl or nitro.

The compound of formula (I) of the present invention has a potential fungicidal activity against typical phytopathogenic organisms of Oomycetes including Pythiaceae, Peronosporaceae, etc., for example, Plasmopara viticola in grapes, Phytophthora infestans in potato and tomato, Phytophthora capsici in red pepper, and the like, and therefore, can be used as an agent for controlling plant diseases caused by such phytopathogenic organisms.

Among the compounds of formula (I), the preferred one includes those wherein $R^1$ and $R^2$ independently of one another represent hydrogen, $(C_1-C_4)$alkyl, $(C_3-C_6)$alkenyl, $(C_3-C_6)$alkynyl, $(C_3-C_6)$cycloalkyl or

$R^3$ represents methyl, ethyl or trifluoromethyl, $R^4$ represents 2-thienyl or 3-thienyl, $R^5$ represents cyano or thiocarbamoyl and $R^6$ represents $(C_1-C_6)$alkyl.

The compound of formula (I) according to the present invention can also exist in the form of an optically active isomer. Therefore, it should be understood that such optical isomer of the compound of formula (I) is included within the scope of the present invention.

In addition, the present invention also relates to a process for preparing the novel 2-aminothiazolecarboxamide derivative having the general formula (I) above. The process of the present invention can be represented by the following synthetic methods (I) and (II).

Synthetic Method (I)

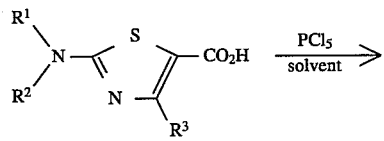

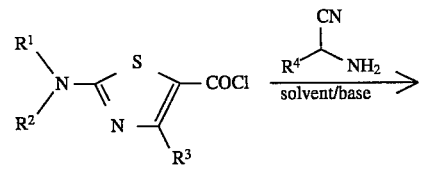

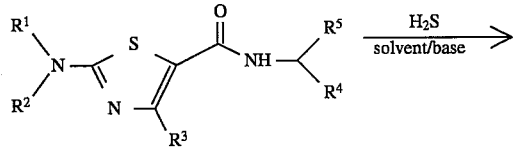

(I) $R^5$ = cyano group

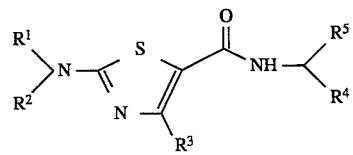

(I)
$R^5$ = thiocarbamoyl group

Synthetic Method (II)

X = halogen atom

-continued
Synthetic Method (II)

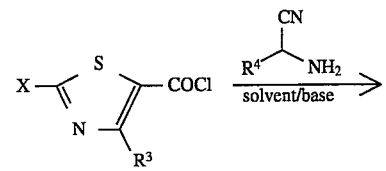

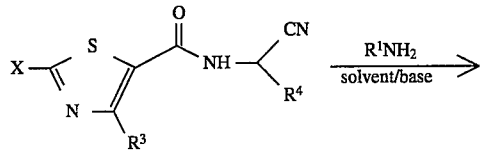

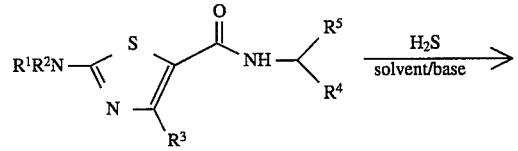

(I)
$R^2$ = hydrogen atom
$R^5$ = cyano group

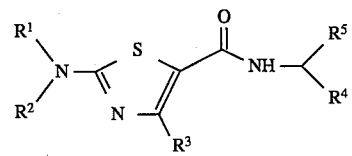

(I)
$R^2$ = hydrogen atom
$R^5$ = thiocarbamoyl group

All the desired compounds of formula (I) of the present invention can be synthesized according to the synthetic method (I) and, the compounds of formula (I) wherein $R^2$ is hydrogen can also be particularly prepared according to the synthetic method (II).

Hereinafter, the synthetic methods of the present invention will be more specifically explained.

Synthetic Method (II)

The compound of formula (I) according to the present invention can be synthesized by the following method.

When in the compound of formula (I) $R^1$ represents alkyl, alkenyl, cycloalkyl, phenyl or benzyl and $R^2$ represents hydrogen, or alkyl which is different from $R^1$, first the intermediate compounds of formulae (4-1) and (4-2) are prepared according to the following reaction scheme (1).

Reaction Scheme (1)

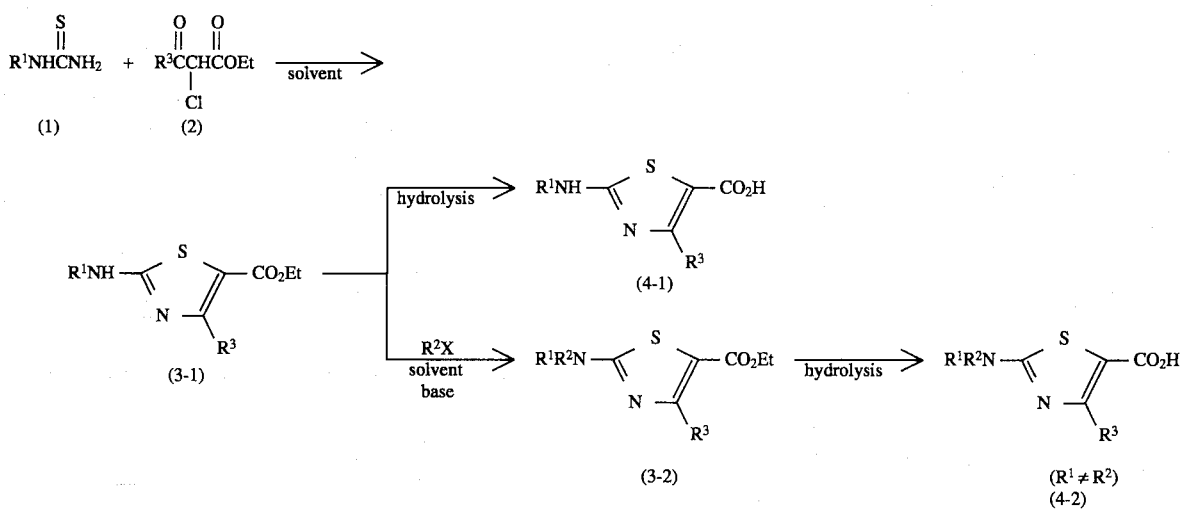

In the above reaction scheme, $R^1$, $R^2$ and $R^3$ are defined as previously described.

The precursor derivative of formula (1) which is used as the starting compound in the above reaction scheme (1) can be prepared from ammonium thiocyanate, benzoyl chloride and primary amine according to the method disclosed in O. S. Coll., Vol. 3, 734; and the precursor derivative of formula (2) which is also used as the starting material in the reaction scheme (1) can be prepared by reacting ethyl β-ketone ester either with sulfuryl chloride (see Synthesis, (1987), p188) or with chlorine.

The compound of formula (3-1) can be obtained by condensing the compound of formula (1) with the compound of formula (2) in the presence of a solvent. As the solvent for this purpose, ketones such as acetone, methylethyl ketone, etc., ethers such as tetrahydrofuran, diethylether, etc., halogenated hydrocarbons such as dichloromethane, 1,2-dichloroethane, chloroform, etc., alcohols such as methanol, ethanol, etc., and the like, can be preferably used. Among them, halogenated hydrocarbon solvents are most preferably used. The reaction can be carried out at the temperature in the range of 40° C. to 120° C. and most preferably at the temperature in the range of 70° C. to 100° C.

The compound of formula (4-1) can be obtained by hydrolysis of the compound of formula (3-1) in the presence of a base. In this hydrolysis reaction, an inorganic base such as sodium hydroxide, potassium hydroxide, etc., is suitable as the base; and as the solvent a mixed solvent of ethers such as tetrahydrofuran, etc., and water or a mixed solvent of alcohols such as methanol, ethanol, etc., and water can be preferably used. This reaction can be practiced at the temperature in the range of 20° C. to 120° C.

When $R^1$ differs from $R^2$, the compound of formula (3-2) can be obtained by reacting the compound of formula (3-1) with various alkyl halides in the presence of a base. As the base which can be preferably used for this purpose, an organic base such as triethylamine, pyridine, etc., or an inorganic base such as sodium carbonate, sodium hydrogen carbonate, potassium carbonate, potassium hydride, sodium hydride, etc., can be mentioned, with sodium hydride being most effective. The solvent which can be used in this reaction includes halogenated hydrocarbons such as dichloromethane, 1,2-dichloroethane, etc., ethers such as tetrahydrofuran, diethylether, etc., amides such as dimethylformamide, dimethylacetamide, etc., and the like.

The compound of formula (4-2) can be prepared by hydrolyzing the compound of formula (3-2) in the same manner as in the hydrolysis of the compound of formula (3-1).

When the compound of formula (I) wherein $R^1$ and $R^2$ represent the same alkyl group, or $R^1$ represents

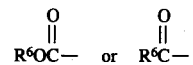

and $R^2$ represents hydrogen is desired, the intermediate compounds of formulae (4-3) and (4-4) can be prepared according to the following reaction scheme (2).

Reaction Scheme (2)

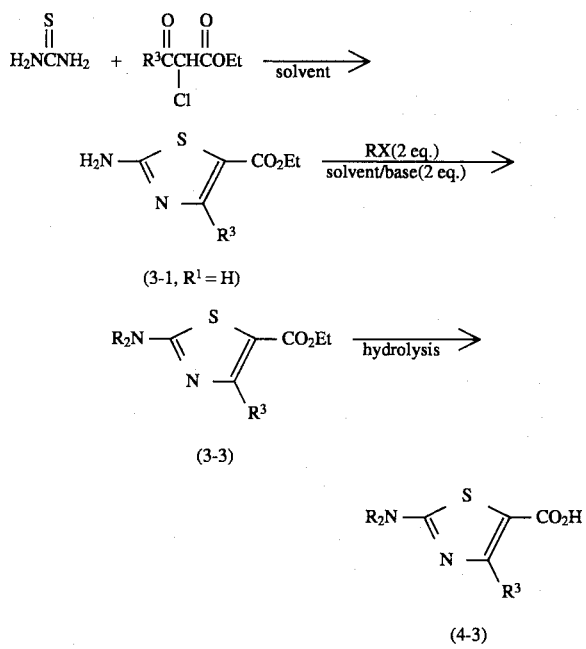

-continued
Reaction Scheme (2)

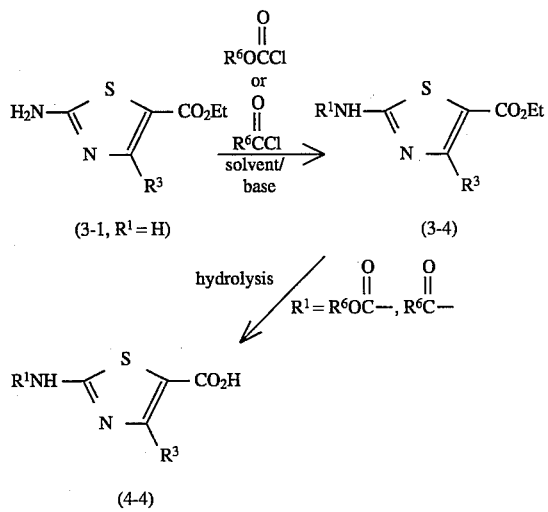

The intermediate compound of formula (4-3) wherein $R^1$ and $R^2$ represent the same radical (R) can be prepared by preparing the compound of formula (3-1) having no substituent on the 2-amino group and reacting the compound of formula (3-1) thus prepared with 2 equivalent weights of the compound of formula RX wherein X represents halogen under the same condition as in the procedure for preparing the compound of formula (3-2) from the compound of formula (3-1) to prepare the compound of formula (3-3) which is then hydrolyzed.

The intermediate compound of formula (4-4) wherein $R^1$ represents

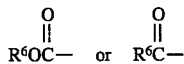

can be prepared by reacting the compound of formula (3-1) having no substituent on the 2-amino group with an alkyl chloroformate

or an acyl halide

to obtain the compound of formula (3-4) which is then hydrolyzed.

Among the final desired compounds of formula (I) according to the present invention, the compound of formula (7) can be prepared from the intermediate compound of formula (4) according to the following reaction scheme (3).

Reaction Scheme (3)

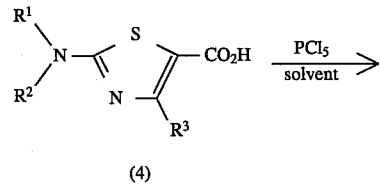

-continued
Reaction Scheme (3)

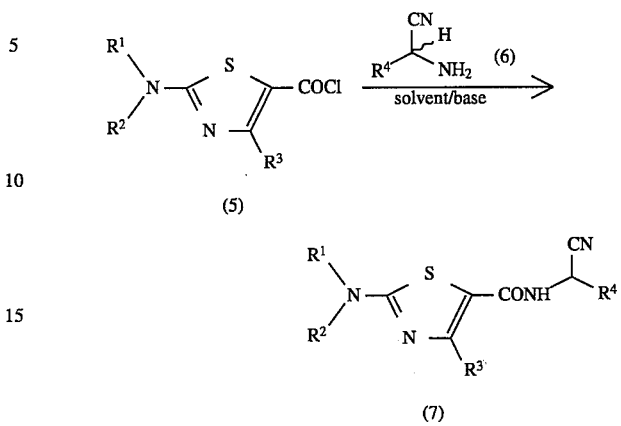

The compound of formula (6) is prepared by stirring an aldehyde in ammonia water in which potassium cyanide and ammonium chloride are dissolved, according to Strecker synthesis (see O. S. Coll., Vol. 3, 84) which is one of the methods for synthesis of α-aminonitriles.

The compound of formula (7) can be prepared by the following procedure. First, the compound of formula (4) is stirred together with thionyl chloride ($SOCl_2$) or phosphorus pentachloride ($PCl_5$) in a solvent, for example, halogenated alkyl hydrocarbons such as dichloromethane, chloroform, etc., aryl hydrocarbons such as benzene, toluene, xylene, etc., and the like, at the temperature in the range of 0° C. to 120° C. to obtain an acid halide of formula (5). The acid halide (5) thus obtained is then reacted with the compound of formula (6) in the presence of a base and a solvent to prepare the compound of formula (7). The base which can be suitably used in this reaction includes an organic base such as triethylamine, pyridine, etc., or an inorganic base such as sodium hydrogen carbonate, sodium carbonate, potassium carbonate, etc.; and as the solvent halogenated hydrocarbons such as dichloromethane, 1,2-dichloroethane, chloroform, carbon tetrachloride, etc., ethers such as tetrahydrofuran, diethylether, etc., ketones such as acetone, methylethyl ketone, etc., nitriles such as acetonitrile, isobutyronitrile, etc., and the like can be preferably used. This reaction can be carried out at the temperature in the range of 0° C. to 80° C.

Synthetic Method (II)

The compound of formula (I) according to the present invention wherein $R^1$ represents alkyl, alkenyl, cycloalkyl or benzyl and $R^2$ represents hydrogen, i.e. the compound of formula (7-1), can be synthesized according to the following method.

Reaction Scheme (4)

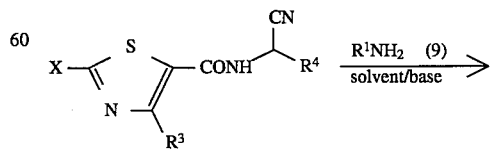

(8)  X = halogen atom

-continued
Reaction Scheme (4)

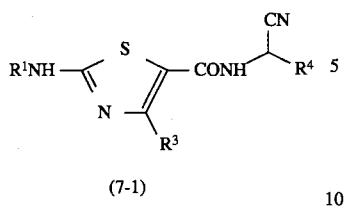

(7-1)

Specifically, the compound of formula (7-1) can be obtained by reacting the compound of formula (8) with various primary amines of formula (9) in the presence of a base and a solvent. As the base suitable for this purpose, an organic base such as triethylamine, pyridine, etc, or an inorganic base such as sodium hydrogen carbonate, sodium carbonate, potassium carbonate, etc., can be used. In addition, when the primary amine which participates in the reaction is used in an excessive amount (2 to 3 times molar amount), this primary amine is used instead of the base. The most preferable base in this reaction is an organic base such as triethylamine. As the solvent halogenated hydrocarbons such as dichloromethane, 1,2-dichloroethane, chloroform, carbon tetrachloride, etc., ethers such as tetrahydrofuran, diethylether, etc., ketones such as acetone, methylethyl ketone, etc., amides such as dimethylformamide, dimethylacetamide, etc., and the like can be used, with ether solvents being most preferable.

In this reaction, the primary amine (9) is used, after any water is removed therefrom, in an amount of 2 to 3 moles with respect to one mole of the compound of formula (8). The reaction according to the reaction scheme (4) can be carried out at the temperature of 20° C. to 100° C.

The derivative of formula (8) which is used as the starting compound in the above reaction can be synthesized by the method disclosed in European Patent No. 313,091, as depicted in the following reaction scheme (5).

Reaction Scheme (5)

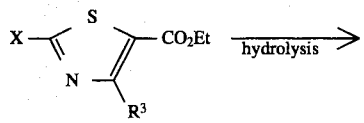

(10)

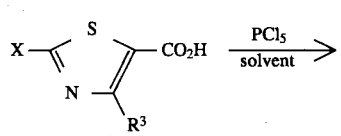

-continued
Reaction Scheme (5)

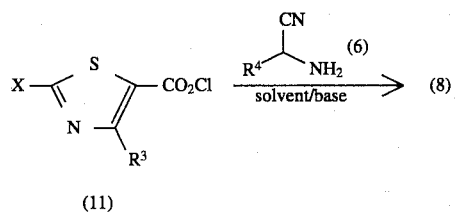

(11)

Specifically, the compound of formula (8) is prepared by hydrolyzing the compound of formula (10), reacting the hydrolyzed product with thionyl chloride ($SOCl_2$) or phosphorus pentachloride ($PCl_5$) to obtain an acid halide of formula (11) which is then reacted with the α-aminonitrile compound of formula (6).

The compound of formula (10) which is used as the starting compound for preparing the compound of formula (8) can be prepared by the method disclosed in J. Heterocylcic Chem., 22, 621 (1985).

The compound of formula (12) which is one of the final desired compound of the present invention can be prepared by the following reaction scheme (6).

Reaction Scheme (6)

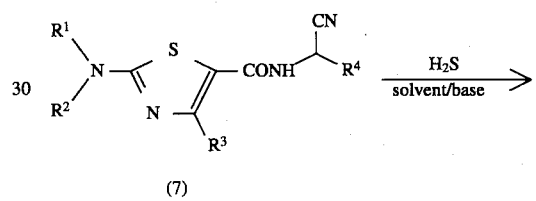

(7)

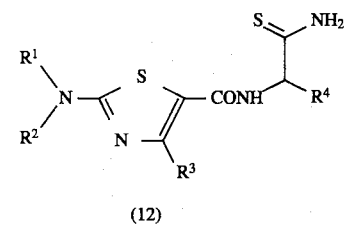

(12)

Specifically, the compound of formula (12) can be prepared by stirring the compound of formula (7) in a base and a solvent while introducing hydrogen sulfide gas into the reaction solution. The suitable base in this reaction includes an organic base such as triethylamine, pyridine, etc., or an inorganic base such as sodium hydrogen carbonate, sodium carbonate, potassium carbonate, etc.; and as the solvent an organic base such as triethylamine, pyridine, etc., is used without any additional solvent or ethers such as tetrahydrofuran, diethylether, etc., halogenated hydrocarbons such as dichloromethane, chloroform, carbon tetrachloride, etc., esters such as ethylformate, ethyl acetate, etc., alcohols such as methanol, ethanol, etc., and the like can also be used. The reaction temperature can be 20° C. to 100° C.

Typical compounds of formula (I) according to the present invention which can be prepared by the synthetic methods as described above are listed in the following Table 1.

TABLE 1

$$\begin{array}{c}\text{R}^1\\\text{R}^2\end{array}\!\!\text{N}\!-\!\!\!\begin{array}{c}\text{S}\\\diagup\!\!\!\diagdown\\\text{N}\end{array}\!\!\!\begin{array}{c}\phantom{x}\\-\!\text{CONH}\!-\!\!\!\begin{array}{c}\text{R}^4\\|\\\text{C}\!-\!\text{H}\\|\\\text{R}^5\end{array}\\\text{R}^3\end{array}\quad\text{(I)}$$

| Comp. No. | R¹ | R² | R³ | R⁴ | R⁵ |
|---|---|---|---|---|---|
| 1 | CH₃— | H | CH₃— | 2-thienyl | —CN |
| 2 | CH₃— | CH₃— | CH₃— | " | —CN |
| 3 | CH₃— | H | CH₃— | " | —C(=S)NH₂ |
| 4 | CH₃— | H | CF₃— | " | —CN |
| 5 | CH₃CH₂— | H | CH₃— | " | —CN |
| 6 | CH₃CH₂— | H | CH₃— | " | —C(=S)NH₂ |
| 7 | CH₃CH₂— | H | CF₃— | " | —CN |
| 8 | (CH₃)₂CH— | H | CH₃— | " | —CN |
| 9 | CH₂=CH—CH₂— | H | CH₃— | 2-thienyl | —CN |
| 10 | CH₂=CH—CH₂— | H | CH₃— | " | —C(=S)NH₂ |
| 11 | CH₂=CH—CH₂— | H | CF₃— | " | —CN |
| 12 | cyclopropyl | H | CH₃— | " | " |
| 13 | " | H | CH₃— | 3-thienyl | " |
| 14 | " | H | CH₃— | 2-thienyl | —C(=S)NH₂ |
| 15 | " | H | CF₃— | " | —CN |
| 16 | " | H | CH₃— | 2-furyl | " |
| 17 | " | H | CH₃— | —Ph | " |
| 18 | (CH₃)₃C— | H | CH₃— | 2-thienyl | —CN |
| 19 | PhCH₂— | H | CH₃— | " | " |
| 20 | " | H | CH₃— | 2-furyl | " |

TABLE 1-continued

Structure (I):

$$R^1R^2N-C(=N-)(S-)=C(R^3)-CONH-CH(R^4)(R^5)$$
(thiazole ring with R³ at 4-position, CONHCHR⁴R⁵ at 5-position, NR¹R² at 2-position)

| Comp. No. | R¹ | R² | R³ | R⁴ | R⁵ |
|---|---|---|---|---|---|
| 21 | PhCH₂— | H | CH₃— | —Ph | " |
| 22 | Ph— | H | CH₃— | 2-thienyl | " |
| 23 | " | H | CH₃— | 2-furyl | " |
| 24 | " | H | CH₃— | —Ph | " |
| 25 | CH₃OC(=O)— | H | CH₃— | 2-thienyl | " |
| 26 | " | H | CH₃— | " | —C(=S)NH₂ |
| 27 | CH₃OC(=O)— | H | CF₃— | 2-thienyl | —CN |
| 28 | " | H | CH₃— | 2-furyl | " |
| 29 | " | H | CH₃— | —Ph | " |
| 30 | CH₃CH₂OC(=O)— | H | CH₃— | 2-thienyl | " |
| 31 | cyclopropyl-C(=O)— | H | CH₃— | —Ph | " |
| 32 | (CH₃)₃CC(=O)— | H | CH₃— | " | " |
| 33 | PhC(=O)— | H | CH₃— | " | " |
| 34 | 2,4-dichlorophenyl-C(=O)— | H | CH₃— | 2-furyl | " |
| 35 | 2,4-dichlorophenyl-C(=O)— | H | CH₃— | —Ph | —CN |
| 36 | CH₃CH₂— | H | CF₃— | 2-thienyl | —C(=S)NH₂ |

TABLE 1-continued

Structure (I):

$$R^1R^2N-C(=N-)-S-C(=C(R^3)-)-CONH-CH(R^4)(R^5)$$ (thiazole ring with R³ at 4-position)

| Comp. No. | $R^1$ | $R^2$ | $R^3$ | $R^4$ | $R^5$ |
|---|---|---|---|---|---|
| 37 | $CH_3CH_2-$ | H | $CH_3CH_2-$ | 2-thienyl | $-CN$ |
| 38 | $CH_3CH_2-$ | H | $CH_3CH_2-$ | 2-thienyl | $-C(=S)NH_2$ |
| 39 | $CH_3-$ | H | $CH_3CH_2-$ | 2-thienyl | $-CN$ |
| 40 | $CH_3-$ | H | $CH_3CH_2-$ | 2-thienyl | $-C(=S)NH_2$ |
| 41 | cyclopropyl | H | $CH_3CH_2-$ | 2-thienyl | $-CN$ |
| 42 | cyclopropyl | H | $CH_3CH_2-$ | 2-thienyl | $-C(=S)NH_2$ |
| 43 | $CH_2=CH-CH_2-$ | H | $CH_3CH_2-$ | 2-thienyl | $-CN$ |

The compound of formula (I) according to the present invention has a potent fungicidal activity against various phytopathogenic organisms, particularly against Oomycetes, and therefore, can be used as an agent for controlling plant diseases caused by such phytopathogenic organisms, for example, Plasmopara viticola in grapes, Phytophthora infestans in potato, Phytophthora capsici in red pepper, etc.

When the compound of formula (I) according to the present invention is used for controlling plant diseases in agricultural fields, the compound of formula (I) is can be prepared in the form of a agricultural composition. Such agricultural composition contains at least one of the compound of formula (I) as an active ingredient, together with a conventional agriculturally acceptable carrier.

The present invention will be more specifically explained by the following preparations and examples. However, it should be understood that the present invention will not be limited to those examples in any manner.

PREPARATION 1

Synthesis of 2-methylamino-4-methyl-thiazole-5-carboxylic acid

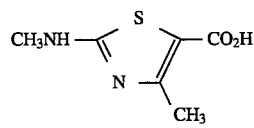

3.6g of methyl thiourea and 7.9g of ethyl 2-chloroacetoacetate were added to 100ml of 1,2-dichloroethane and the mixture was stirred under reflux for 10 hours. After removing the solvent under reduced pressure, 10% aqueous sodium hydroxide solution was added thereto to recrystallize the resulting product which was then filtered to obtain 7.8g (Yield 96%) of ethyl 2-methylamino-4-methyl-thiazole-5-carboxylate as a pale yellow solid. The obtained solid product was dissolved in 60ml of a mixed solvent of methanol-distilled water (v/v=3/1) containing 1.8g of sodium hydroxide. The reaction mixture was stirred under reflux for 8 hours, evaporated under reduced pressure to remove methanol and then adjusted to pH 2 to 3 by adding 10% aqueous hydrochloric acid solution to precipitate the white solid. The precipitated solid product was filtered, washed with water and diethylether and then dried to obtain 6.0g (Yield 90%) of the title compound as a white solid.

$^1$H-NMR (DMSO-$d_6$): δ 12.4(1H, br), 3.0(3H, s), 2.40(3H, s)

PREPARATION 2

Synthesis of 2-dimethylamino-4-methyl-thiazole-5-carboxylic acid

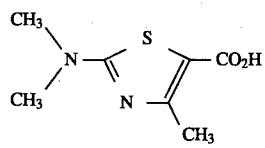

1.6g of ethyl 2-amino-4-methyl-thiazole-5-carboxylate and 0.68g of sodium hydride (purity 60%) were dissolved in 20ml of dry tetrahydrofuran and then 2.4ml of iodomethane was added thereto at 0° C. The reaction mixture was stirred for one hour at normal temperature and then extracted with water and ethylacetate. The extract was dried over anhydrous magnesium sulfate and evaporated to obtain 1.6g (Yield 89%) of ethyl 2-dimethylamino-4-methyl-thiazole-5-carboxylate as a white solid. The resulting product was added to 60ml of a mixed solvent of tetrahydrofuran-water (v/v=2/1) containing 1.2g of sodium hydroxide. The reaction mixture was stirred for 16 hours at normal temperature and then treated according to the same procedure as PREPARATION 1 to obtain 1.3g (Yield 86%) of the title compound as a white solid.

$^1$H-NMR (DMSO-$d_6$): δ 11.8(1H, br), 3.3(6H, s), 2.50(3H, s)

PREPARATION 3

Synthesis of 2-methoxycarbonylamino-4-methyl-thiazole-5-carboxylic acid

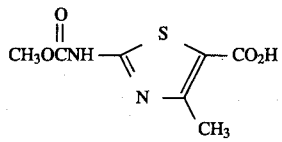

2.0g of ethyl 2-amino-4-methyl-thiazole-5-carboxylate and 2.7ml of triethylamine were dissolved in 40ml of dichloromethane and then 1.1ml of methyl chloroformate was added thereto at 0° C. The reaction mixture was stirred for 6 hours at normal temperature, evaporated to remove the solvent and then extracted with 10% aqueous sodium hydroxide solution and ethylacetate. The organic layer was separated, dried over anhydrous magnesium sulfate and then evaporated to obtain 2.1g (Yield 81%) of ethyl 2-methoxycarbonylamino-4-methyl-thiazole-5-carboxylate as a pale yellow solid. The resulting product was hydrolyzed according to the same procedure as PREPARATION 1 to obtain 1.4g (Yield 75%) of the title compound as a pale yellow solid.

$^1$H-NMR (DMSO-$d_6$): δ 12.3(1H, s, br), 3.80(3H, s), 2.50(3H, s)

PREPARATION 4

Synthesis of 2-bromo-4-trifluoromethyl-thiazole-5-carboxylic acid (cyano-thiophen-2-yl-methyl)-amide

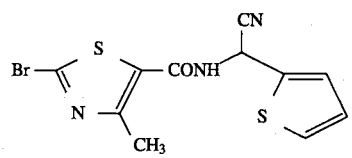

1.2g of 2-bromo-4-trifluoromethyl-thiazole-5-carboxylic acid and 1.0g of phosphorus pentachloride were added to 10ml of dichloromethane and then stirred under reflux for one hour. After removing the solvent and phosphorus oxychloride under reduced pressure, the residue was dissolved again in 10ml of dichloromethane and 0.84g of amino-thiophen-2-yl-acetonitrile hydrochloride and 1.3ml of triethylamine were added thereto at 0° C. The reaction mixture was stirred for 2 hours at normal temperature. Water was added to the reaction mixture and the organic layer was separated. The separated organic layer was dried over anhydrous magnesium sulfate and then evaporated. The residue was then subjected to silica gel column chromatography to obtain 1.2g (Yield 70%) of the title compound.

$^1$H-NMR (CDCl$_3$): δ 7.42(1H, d), 7.35(1H, d), 7.06(1H, t), 6.40(1H, d, br), 6.25(1H, br)

PREPARATION 5

Synthesis of 2-bromo-4-ethyl-thiazole-5-carboxylic acid (cyano-thiophen-2-yl-methyl)-amide

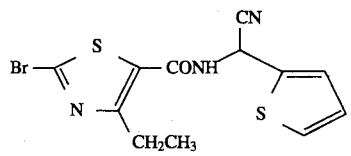

According to the same procedure as PREPARATION 4 except that 1.5g of 2-bromo-4-ethyl-thiazole-5-carboxylic acid is used instead of 2-bromo-4-trifluoromethyl-thiazole-5-carboxylic acid, 1.68g (Yield 75%) of the title compound was obtained.

$^1$H-NMR (CDCl$_3$): δ 7.41(1H, d), 7.34(1H, d), 7.05(1H, t), 6.40(2H, br)

EXAMPLE 1

Synthesis of 2-methylamino-4-methyl-thiazole-5-carboxylic acid (cyano-thiophen-2-yl-methyl)-amide (1)

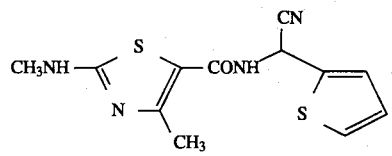

1.8g of 2-methylamino-4-methyl-thiazole-5-carboxylic acid and 2.4g of phosphorus pentachloride were added to 20ml of dichloromethane and then stirred under reflux for one hour. After removing the solvent and phosphorus oxychloride under reduced pressure, the residue was dissolved again in 20ml of dichloromethane and 2.0g of amino-thiophen-2-yl-acetonitrile hydrochloride and 4.8ml of triethylamine were added thereto 0° C. The reaction mixture was stirred for 2 hours at normal temperature and then the solvent was removed under reduced pressure. The residue was extracted with 10% aqueous sodium hydroxide solution and ethylacetate. The organic layer was separated, dried over anhydrous magnesium sulfate and then evaporated. The residue was then subjected to silica gel column chromatography and then the desired fraction was recrystallized from n-hexane and ethylacetate to obtain 1.05g (Yield 34%) of the title compound.

$^1$H-NMR (CDCl$_3$): δ 7.39(1H, d), 7.34(1H, d), 7.04(1H, t), 6.43(1H, d), 5.97(1H, d), 5.90(1H, s, br), 3.0(3H, s), 2.55(3H, s)

EXAMPLE 2

Synthesis of
2-dimethylamino-4-methyl-thiazole-5-carboxylic
acid (cyano-thiophen-2-yl-methyl) -amide (2)

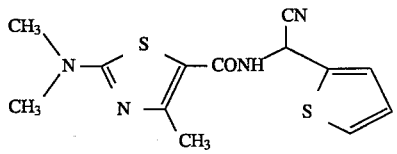

1.2g of 2-dimethylamino-4-methyl-thiazole-5-carboxylic acid was converted into 2-dimethylamino-4-methyl-thiazole-5-carboxylic acid chloride using 1.3g of phosphorus pentachloride according to the same procedure as EXAMPLE 1. Then 1.1g of amino-thiophen-2-yl-acetonitrile hydrochloride and 2.5ml of triethylamine were added thereto and the reaction mixture was treated according to the same procedure as EXAMPLE 1 to obtain 0.65g (Yield 36%) of the title compound.

$^1$H-NMR (CDCl$_3$): δ 7.39(1H, d), 7.34(1H, d), 7.04(1H, t), 6.42(1H, d), 6.00(1H, d), 3.13(6H, s), 2.56(3H, s)

EXAMPLE 3

Synthesis of
2-ethylamino-4-methyl-thiazole-5-carboxylic acid
(cyano-thiophen-2-yl-methyl)-amide (5)

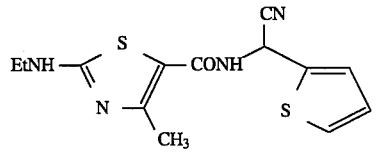

1.2g of 2-ethylamino-4-methyl-thiazole-5-carboxylic acid was converted into 2-ethylamino-4-methyl-thiazole-5-carboxylic acid chloride using 1.3g of phosphorus pentachloride according to the same procedure as EXAMPLE 1. Then 1.1g of amino-thiophen-2-yl-acetonitrile hydrochloride and 2.5ml of triethylamine were added thereto and the reaction mixture was treated according to the same procedure as EXAMPLE 1 to obtain 0.57g (Yield 32%) of the title compound.

$^1$H-NMR (CDCl$_3$): δ 7.36(1H, d), 7.30(1H, d), 7.04(1H, t), 6.10(1H, d), 5.99(1H, s, br), 3.28(2H, q), 2.53(3H, s), 1.30(3H, t)

EXAMPLE 4

Synthesis of
2-cyclopropylamino-4-methyl-thiazole-5-carboxylic
acid (cyano-thiophen-2-yl-methyl)-amide (12)

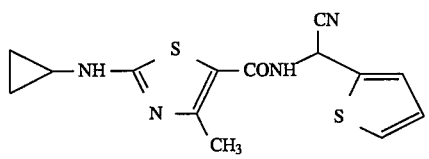

1.7g of 2-cyclopropylamino-4-methyl-thiazole-5-carboxylic acid was converted into 2-cyclopropylamino-4-methyl-thiazole-5-carboxylic acid chloride using 1.9g of phosphorus pentachloride according to the same procedure as EXAMPLE 1. Then 1.7g of amino-thiophen-2-yl-acetonitrile hydrochloride and 3.9ml of triethylamine were added thereto and the reaction mixture was treated according to the same procedure as EXAMPLE 1 to obtain 1.0g (Yield 39%) of the title compound.

$^1$H-NMR (CDCl$_3$): δ 7.40(1H, d), 7.34(1H, d), 7.05(1H, t), 6.60(1H, s), 6.45(1H, d), 6.00(1H, d), 2.59(1H, m), 2.54(3H, s), 0.80(4H, m)

EXAMPLE 5

Synthesis of
2-t-butylamino-4-methyl-thiazole-5-carboxylic acid
(cyano-thiophen-2-yl-methyl)-amide (18)

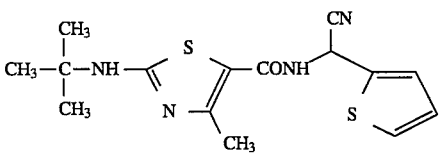

1.5g of 2-t-butylamino-4-methyl-thiazole-5-carboxylic acid was converted into 2-t-butylamino-4-methyl-thiazole-5-carboxylic acid chloride using 1.6g of phosphorus pentachloride according to the same procedure as EXAMPLE 1. Then 1.4g of amino-thiophen-2-yl-acetonitrile hydrochloride and 3.3ml of triethylamine were added thereto and the reaction mixture was treated according to the same procedure as EXAMPLE 1 to obtain 0.96g (Yield 41%) of the title compound.

$^1$H-NMR (CDCl$_3$): δ 7.38(1H, d), 7.34(1H, d), 7.04(1H, t), 6.44(1H, d), 6.00(1H, d), 5.56(1H, s, br), 2.52(3H, s), 1.42(9H, s)

EXAMPLE 6

Synthesis of
2-methoxycarbonylamino-4-methyl-thiazole-5-carboxylic acid (cyano-thiophen-2-yl-methyl)-amide (25)

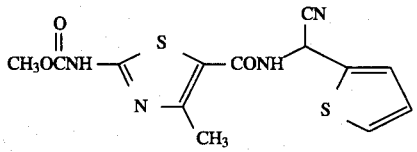

1.7g of 2-methoxycarbonylamino-4-methyl-thiazole-5-carboxylic acid was converted into 2-methoxycarbonylamino-4-methyl-thiazole- 5-carboxylic acid chloride using 1.8g of phosphorus pentachloride according to the same procedure as EXAMPLE 1. Then 1.5g of amino-thiophen-2-yl-acetonitrile hydrochloride and 2.4ml of triethylamine were added thereto and the reaction mixture was treated according to the same procedure as EXAMPLE 1 to obtain 0.85g (Yield 32%) of the title compound.

$^1$H-NMR (CDCl$_3$): δ 10.5(1H, s), 7.41(1H, d), 7.35(1H, d), 7.06(1H, t), 6.41(1H, d), 6.18(1H, d), 3.89(3H, s), 2.66(3H, s)

The compound Nos. 8, 9, 19, 22 and 30 were synthesized according to the same procedure as EXAMPLES 1 to 6. $^1$H-NMR data of the synthesized compounds are described in the following Table 2.

TABLE 2

| Comp. No. | $^1$H-NMR (solvent) : δ |
|---|---|
| 8 | (CDCl$_3$): 7.38(1H, d), 7.30(1H, d), 7.00(1H, t), 6.44 (1H, d), 6.00(1H, d), 5.49(1H, s, br), 3.61 (1H, m), 2.52(3H, s), 1.27(6H, m) |
| 9 | (CDCl$_3$): 7.38(1H, d), 7.32(1H, d), 7.04(1H, t), 6.50 (1H, s, br), 6.42(1H, d), 6.01(1H, d), 5.85 (1H, m), 5.30(1H, d), 5.25(1H, M), 3.88(2H, m), 2,53(3H, s) |
| 19 | (CDCl$_3$): 7.35(7H, m), 7.04(1H, t), 6.42(1H, d), 6.25 (1H, s), 5.95(1H, d), 4.46(2H, s), 2.51(3H, s) |
| 22 | (CDCl$_3$): 8.40(1H, s), 7.35(6H, m), 7.20(1H, t), 7.00 (1H, s), 6.40(1H, d), 6.00(1H, d), 2.55(3H, s) |
| 30 | (CDCl$_3$): 10.70(1H, s, br), 7.37(1H, d), 7.30(1H, d), 7.05(1H, t), 6.39(1H, d), 6.20(1H, d), 4.30 (2H, q), 2.67(3H, s), 1.34(3H, t) |

EXAMPLE 7

Synthesis of
2-cyclopropylamino-4-methyl-thiazole-5-carboxylic acid (cyano-thiophen-3-yl-methyl)-amide (13)

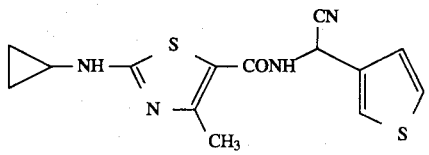

1.4g of 2-cyclopropylamino-4-methyl-thiazole-5-carboxylic acid was converted into 2-cyclopropylamino-4-methyl-thiazole-5-carboxylic acid chloride using 1.6g of phosphorus pentachloride according to the same procedure as EXAMPLE 1. Then 1.4g of amino-thiophen-3-yl-acetonitrile hydrochloride and 3.2ml of triethylamine were added thereto and the reaction mixture was treated according to the same procedure as EXAMPLE 1 to obtain 0.73g (Yield 35%) of the title compound.

$^1$H-NMR (CDCl$_3$): δ 7.54(1H, s), 7.40(1H, m), 7.20(2H, m), 6.92(1H, s), 6.30(1H, d), 2.60(1H, m), 2.53(3H, s), 0.80(4H, m)

EXAMPLE 8

Synthesis of
2-cyclopropylamino-4-methyl-thiazole-5-carboxylic acid (cyano-furan-2-yl-methyl)-amide (16)

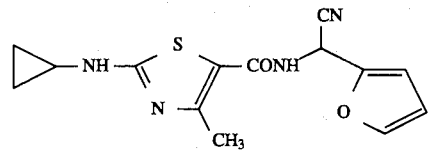

1.4g of 2-cyclopropylamino-4-methyl-thiazole-5-carboxylic acid was converted into 2-cyclopropylamino-4-methyl-thiazole-5-carboxylic acid chloride using 1.6g of phosphorus pentachloride according to the same procedure as EXAMPLE 1. Then 1.2g of amino-furan-2-yl-acetonitrile hydrochloride and 3.2ml of triethylamine were added thereto and the reaction mixture was treated according to the same procedure as EXAMPLE 1 to obtain 0.83g (Yield 35%) of the title compound.

$^1$H-NMR (CDCl$_3$): δ 7.48(1H, d), 6.80(1H, s), 6.58(1H, d), 6.43(1H, t), 6.32(1H, d), 6.00(1H, d), 2.60(1H, m), 2.55(3H, s), 0.85(4H, m)

The compound Nos. 20, 23, 28 and 34 were synthesized according to the same procedure as EXAMPLE 8. $^1$H-NMR data of the synthesized compounds are described in the following Table 3.

TABLE 3

| Comp. No. | $^1$H-NMR (solvent) : δ |
|---|---|
| 20 | (CDCl$_3$): 7.30(6H, m), 6.60(2H, m), 6.45(1H, s), 6.25 (1H, d), 5.95(1H, d), 4.45(2H, s), 2.50(3H, s) |
| 23 | (CDCl$_3$): 8.20(1H, s), 7.40(5H, m), 7.16(1H, m), 6.57 (1H, t), 6.42(1H, d), 6.30(1H, d), 6.00(1H, d), 2.57(3H, s) |
| 28 | (CDCl$_3$): 9.90(1H, s), 7.49(1H, s), 6.59(1H, d), 6.44 (1H, s), 6.27(1H, d), 6.15(1H, d), 3.89(3H, s), 2.64(3H, s) |
| 34 | (CDCl$_3$): 10.00(1H, s, br), 7.95(1H, d), 7.45(3H, m), 6.60(1H, s), 6.50(1H, s), 6.28(1H, d), 6.20 (1H, d) , 2. 65 (3H, s) |

EXAMPLE 9

Synthesis of
2-benzylamino-4-methly-thiazole-5-carboxylic acid
(cyano-phenyl-methyl)-amide (21)

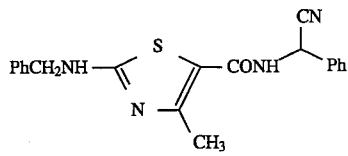

1.2g of 2-benzylamino-4-methyl-thiazole-5-carboxylic acid was converted into 2-benzylamino-4-methyl-thiazole-5-carboxylic acid chloride using 1.1g of phosphorus pentachloride according to the same procedure as EXAMPLE 1. Then 0.89g of amino-phenylacetonitrile hydrochloride and 2.3ml of triethylamine were added thereto and the reaction mixture was treated according to the same procedure as EXAMPLE 1 to obtain 0.68g (Yield 39%) of the title compound.

$^1$H-NMR (CDCl$_3$): δ 7.40(10H, m), 6.25(1H, d), 6.15(1H, s, br), 5.80(1H, d), 4.45(2H, s), 2.52(3H, s)

The compound Nos. 17, 24, 29, 31, 32, 33 and 35 were synthesized according to the same procedure as EXAMPLE 9. $^1$H-NMR data of the synthesized compounds are described in the following Table 4.

TABLE 4

| Comp. No. | $^1$H-NMR (solvent) : δ |
|---|---|
| 17 | (CDCl$_3$): 7.46(5H, m), 7.28(1H, s), 6.29(1H, d), 5.95 (1H, d), 2.60(1H, m), 2.53(3H, s), 0.83(4H, m) |
| 24 | (CDCl$_3$): 8.0(1H, s, br), 7.30(9H, m), 7.15(1H, t), 6.25(1H, d), 5.85(1H, d), 2.55(3H, s) |
| 29 | (CDCl$_3$): 10.00(1H, s), 7.50(5H, m), 6.23(1H, d), 6.00(1H, d), 3.88(3H, s), 2.65(3H, s) |
| 31 | (CDCl$_3$): 9.40(1H, s), 7.50(5H, m), 6.20(1H, d), 6.00 (1H, d), 2.70(1H, m), 2.65(3H, s), 1.20(4H, m) |
| 32 | (CDCl$_3$): 8.90(1H, s), 7.50(5H, m), 6.20(1H, d), 6.00 (1H, d), 2.65(3H, s), 1.30(9H, s) |
| 33 | (CDCl$_3$): 7.90(2H, m), 7.65(9H, m), 6.20(1H, d), 6.15 (1H, d), 2.60(3H, s) |
| 35 | (CDCl$_3$): 10.1(1H, s, br), 7.90(1H, d), 7.50(7H, m), 6.25(1H, d), 6.15(1H, d), 2.60(3H, s) |

EXAMPLE 10

Synthesis of
2-ethylamino-4-trifluoromethyl-thiazole-5-carboxylic
acid (cyano-thiophen-2-yl-methyl)-amide (7)

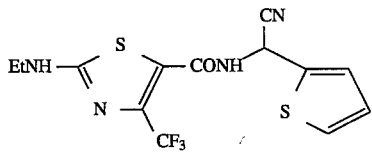

1.0g of 2-bromo-4-trifluoromethyl-thiazole-5-carboxylic acid (cyano-thiophen-2-yl-methyl)-amide, 0.36ml of triethylamine and 0.50ml of ethylamine were added to 10ml of tetrahydrofuran and the reaction mixture was stirred under reflux for 4 hours. Water and ethylacetate were added thereto to separate the layers. The separated organic layer was dried over anhydrous sodium sulfate and evaporated. The residue was recrystallized from the mixed solvent of n-hexane and ethylacetate to obtain 0.67g (Yield 73%) of the title compound.

$^1$H-NMR (CDCl$_3$): δ 7.42(1H, d), 7.34(1H, d), 7.06(1H, t), 6.59(1H, s, br), 6.34(1H, d), 5.69(1H, s, br), 3.32(2H, q), 1.33(3H, t)

EXAMPLE 11

Synthesis of
2-ethylamino-4-ethyl-thiazole-5-carboxylic acid
(cyano-thiophen-2-yl-methyl)-amide (37)

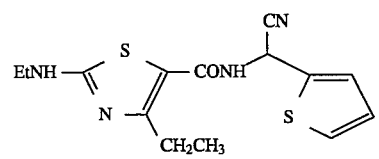

1.0g of 2-bromo-4-ethyl-thiazole-5-carboxylic acid (cyano-thiophen- 2-yl-methyl)-amide, 0.40ml of triethylamine and 0.55ml of ethylamine were added to 10ml of tetrahydrofuran. The reaction mixture was stirred under reflux for 4 hours and then treated according to the same procedure as EXAMPLE 10 to obtain 0.63g (Yield 70%) of the title compound.

$^1$H-NMR (CDCl$_3$): δ 7.39(1H, d), 7.33(1H, d), 7.05(1H, t), 5.90(1H, d), 5.50(1H, s, br), 3.28(2H, m), 2.92(2H, q), 1.28(6H, m)

EXAMPLE 12

Synthesis of
2-methylamino-4-ethyl-thiazole-5-carboxylic acid
(cyano-thiophen-2-yl-methyl)-amide (39)

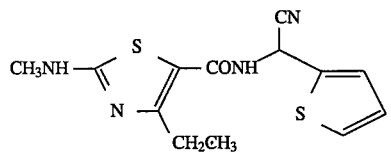

1.0g of 2-bromo-4-ethyl-thiazole-5-carboxylic acid (cyano-thiophen- 2-yl-methyl)-amide, 0.40ml of triethylamine and 0.58ml of methylamine were added to 10ml of tetrahydrofuran. The reaction mixture was stirred under reflux for 4 hours and then treated according to the same procedure as EXAMPLE 10 to obtain 0.77g (Yield 89%) of the title compound.

$^1$H-NMR (CDCl$_3$): δ 7.58(1H, d), 7.38(1H, d), 7.30(1H, d), 7.03(1H, t), 6.94(1H, s, br), 6.43(1H, d), 2.98(2H, q), 2.95(3H, s), 1.25(3H, t)

EXAMPLE 13

Synthesis of
2-allylamino-4-ethyl-thiazole-5-carboxylic acid
(cyano-thiophen-2-yl-methyl)-amide (43)

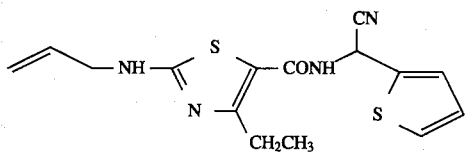

1.0g of 2-bromo-4-ethyl-thiazole-5-carboxylic acid (cyano-thiophen- 2-yl-methyl)-amide, 0.40ml of triethylamine and 0.66ml of allylamine were added to 10ml of tetrahydrofuran. The reaction mixture was stirred under reflux for 12 hours and then treated according to the same procedure as EXAMPLE 10 to obtain 0.57g (Yield 61%) of the title compound.

$^1$H-NMR (CDCl$_3$): δ 7.36(1H, d), 7.30(1H, t), 6.95(1H, d), 6.50(1H, s, br), 6.43(1H, d), 5.86(1H, m), 5.29(1H, d), 5.25(1H, d), 3.90(2H, m), 2.99(2H, q), 1.25(3H, t)

The compound Nos. 11, 15 and 41 were synthesized according to the same procedure as EXAMPLES 10 to 13. $^1$H-NMR data of the synthesized compounds are described in the following Table 5.

TABLE 5

| Comp. No. | $^1$H-NMR (solvent) : δ |
|---|---|
| 11 | (CDCl$_3$): 7.41(1H, d), 7.33(1H, d), 7.05(1H, t), 6.60 (1H, s, br), 5.83(1H, m), 5.32(1H, d), 5.28 (1H, d), 3.90(2H, m) |
| 15 | (CDCl$_3$): 7.30(1H, d), 7.36(1H, d), 7.06(1H, t), 6.59 (1H, s, br), 6.38(1H, d), 6.28(1H, s), 2.64 (1H, m) , 0. 8 0 (4H, m) |
| 41 | (CDCl$_3$): 7.75(1H, d) 7.36(1H, d), 7.31(1H, d), 7.09 (1H, s, br), 7.02(1H, t), 6.45(1H, d), 2.97 (2H, q), 2.56(1H, m), 1.24(3H, t), 0.72(4H, m) |

EXAMPLE 14

Synthesis of
2-ethylamino-4-methyl-thiazole-5-carboxylic acid
(thiocarbamoyl-thiophen-2-yl-methyl)-amide (6)

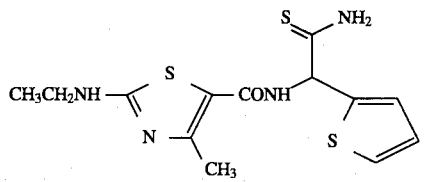

0.85g of 2-ethylamino-4-methyl-thiazole-5-carboxylic acid (cyano-thiophen-2-yl-methyl)-amide (5) was dissolved in 2ml of pyridine and the reaction solution was stirred for 6 hours at 60° C. while introducing hydrogen sulfide gas. After removing the pyridine, the residue was recrystallized from ethylacetate to obtain 0.86g (Yield 91%) of the title compound.

$^1$H-NMR (Acetone-d$_6$): δ 9.25(2H, s, br), 7.56(1H, d), 7.35(1H, d), 7.22(1H, d), 7.14(1H, s), 6.95(1H, t), 6.26(1H, d), 3.33(2H, m), 2.49(3H, s), 1.23(3H, t)

EXAMPLE 15

Synthesis of
2-cyclopropylamino-4-methyl-thiazole-5-carboxylic
acid (thiocarbamoyl-thiophen-2-yl-methyl)-amide
(14)

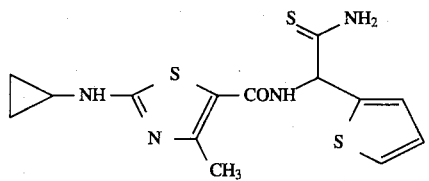

0.72g of 2-cyclopropylamino-4-methyl-thiazole-5-carboxylic acid (cyano-thiophen-2-yl-methyl)-amide (12) was dissolved in 10ml of ethanol and then 0.63ml of triethylamine was added thereto. The reaction solution was stirred under reflux for 8 hours while introducing hydrogen sulfide gas. After removing the solvent, water was added to the residue and then the solid product which is not dissolved in water was filtered. The filtered solid product was washed with diethylether and then dried to obtain 0.70g (Yield 88%) of the title compound.

$^1$H-NMR (CDCl$_3$): δ 9.00(1H, s), 8.46(1H, s), 7.60(1H, d), 7.23(2H, m), 6.93(1H, t), 6.75(1H, s), 6.30(1H, d), 2.58(1H, m), 2.56(3H, s), 0.80(4H, m)

The compound Nos. 3, 10, 26, 36, 38, 40 and 42 were synthesized according to the same procedure as EXAMPLE 15. $^1$H-NMR data of the synthesized compounds are described in the following Table 6.

TABLE 6

| Comp. No. | $^1$H-NMR (solvent) : δ |
|---|---|
| 3 | (Acetone-d$_6$): 9.20(2H, s, br), 7.55(1H, d), 7.34 (1H, d), 7.33(1H, d), 7.22(1H, s, br), 6.94(1H, t), 6.25(1H, d), 2.94(3H, s), 2.49(3H, s) |
| 10 | (Acetone-d$_6$): 9.20(2H, s, br), 7.56(1H, d), 7.33(1H, d), 7.22(1H, d), 6.94(1H, t), 6,.23(1H, d), 5.90(1H, m), 5.25(1H, d), 5.12(1H, d), 3.97 (2H, m), 2.49(3H, s) |
| 26 | (Acetone-d$_6$): 10.7(1H, s, br), 9.25(2H, s, br), 7.88 (1H, d), 7.37(1H, d), 7.26(1H, d), 6.96(1H, t), 6.27(1H, t), 3.82(3H, s), 2.60(3H, s) |
| 36 | (Acetone-d$_6$): 9.16(1H, s), 8.76(1H, s), 7.98(1H, d), 7.35(2H, m), 7.21(1H, m), 6.93(1H, s), 6.25 (1H, d), 3.26(2H, q), 1.26(3H, t) |
| 38 | (Acetone-d$_6$)): 9.24(2H, d, br), 7.53(1H, d), 7.34(1H, d), 7.21(1H, d), 7.10(1H, s), 6.95(1H, t), 6.23(1H, d), 3.38(2H, m), 2.90(2H, q), 1.20 (6H, m) |
| 40 | (Acetone-d$_6$): 9.24(2H, d, br), 7.54(1H, d), 7.34(1H, d), 7.21(1H, d), 7.10(1H, s), 6.94(1H, t), 6.23(1H, d), 2.90(5H, M), 1.20(3H, t) |
| 42 | (Acetone-d$_6$): 9.24(2H, d, br), 7.65(2H, m), 7.36(2H, d), 7.25(2H, d), 6.97(1H, t), 6.28(1H, d), 2.94(2H, q), 2.62(1H, m), 1.22(3H, t), 0.74 (4H, m) |

Biological Test

Assay for determination of the fungicidal activity
against phytopathogenic organisms To identify the fungicidal effect of the compound of the present invention the activity against tomato late blight (Phytophthora infestans) and grape downey mildew (Plasmopara viticola) was determined.

Test 1

Preventive activity against tomato late blight

To determine the preventive activity the desired compound of the present invention was dissolved in 10% acetone solution and Tween-20 was added thereto in the concentration of 250ppm to prepare the test solution. The test solution was sprayed on tomato seedlings which were cultivated for 4 weeks in a greenhouse. Tomato seedlings on which the test solution was sprayed were allowed to stand for 24 hours at room temperature to evaporate the solvent and water. Then, the sporocyte suspension ($10^5$/ml) of Phytophthora infestans which is the causative organism of tomato late blight was inoculated onto leaves of the tomato plants. After 4 days, the state of tomato leaves was observed and compared with the state of the untreated group.

As the comparative drug dimethomorph having the following formula (VI) was used.

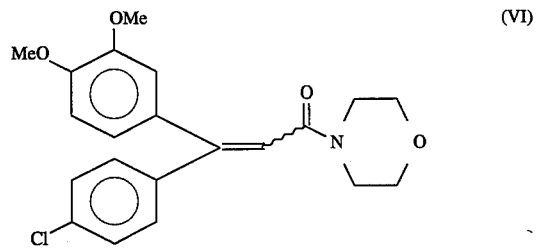
(VI)

The state of tomato leaves was graded according to the following standard and described in the following Table 7.

| Inhibition of development of plant disease | Grade |
|---|---|
| ≧90% | A |
| 60–89% | B |
| ≦59% | C |

TABLE 7

| Comp. No. | Concentration (ppm) | | | |
|---|---|---|---|---|
| | 31 | 16 | 8 | 4 |
| 1 | A | B | B | — |
| 2 | A | B | B | C |
| 3 | A | B | C | — |
| 5 | A | A | A | A |
| 6 | A | A | A | A |
| 7 | C | — | — | — |
| 8 | A | B | C | — |
| 9 | A | A | A | A |
| 10 | A | A | B | B |
| 12 | A | A | B | C |
| 15 | C | — | — | — |
| 18 | B | C | — | — |
| 19 | C | — | — | — |
| 22 | C | — | — | — |
| 25 | A | A | B | C |
| 26 | A | A | B | C |
| 30 | A | B | C | — |
| 37 | A | A | A | A |
| 39 | A | A | — | B |
| 41 | A | A | — | B |
| 43 | A | A | — | B |
| Dimethomorph | A | A | B | C |

Test 2

Systemic activity against tomato late blight

The test solution having a given concentration which was prepared according to the same method as in TEST 1 was injected in an amount of 5 ml into each pot (5cm×5cm) containing tomato seedlings which were cultivated for approximately 4 weeks in a greenhouse. Then, the treated tomato seedlings were allowed to stand for 24 hours to evaporate the solvent. The sporocyte suspension ($10^5$/ml) of the causative organism of tomato late blight was inoculated on the leaves of the tomato. The inoculated tomato leaves were maintained at 20° C. and 100% relative humidity (RH) for 4 days to induce tomato late blight. Then, the development of tomato late blight was observed and compared with that in the untreated group to calculate the ratio of inhibiting the development of tomato late blight. The result is described in the following Table 8.

TABLE 8

| Concentration | Compound | | |
|---|---|---|---|
| (ppm) | 5 | 9 | Dimethomorph |
| 250 | 93 | 67 | 60 |
| 63 | 58 | 0 | 25 |

TEST 3

Curative activity against grape downey mildew

The curative activity of the compound of the present invention against grape downey mildew (Plasmopara viticola) was determined and then described in the following Table 9. The activity was graded A, B and C on the same standard as in TEST 1.

TABLE 9

| Concentration | Compound | | | | | |
|---|---|---|---|---|---|---|
| (ppm) | 1 | 2 | 5 | 9 | 12 | 25 |
| 31 | B | B | A | A | A | C |

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A novel 2-aminothiazolecarboxamide derivative represented by the following general formula (I):

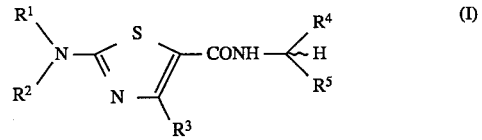
(I)

in which $R^1$ and $R^2$ independently of one another represent hydrogen, ($C_1$-$C_5$)alkyl, ($C_1$-$C_5$)haloalkyl, ($C_3$-$C_6$)alkenyl, ($C_3$-$C_6$)alkynyl, ($C_3$-$C_6$)cycloalkyl,

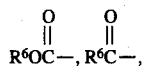

or phenyl or benzyl, each of which may be substituted with halogen, $(C_1-C_3)$alkyl or nitro;

$R^3$ represents $(C_1-C_3)$alkyl or $(C_1-C_3)$haloalkyl;

$R^4$ represents 2-thienyl, 3-thienyl, 2-furyl, 3-furyl, phenyl, or benzyl, each of which may be substituted with halogen, $(C_1-C_6)$alkyl or nitro;

$R^5$ represents cyano or thiocarbamoyl; and $R^6$ represents $(C_1-C_6)$alkyl, $(C_3-C_6)$alkenyl, $(C_3-C_6)$cycloalkyl, or benzyl, each of which may be substituted with halogen, $(C_1-C_3)$alkyl or nitro.

2. The compound of formula (I) according to claim 1 wherein the compound is in the form of an optically active isomer.

3. The compound of formula (I) according to claim 1 wherein $R^1$ and $R^2$ independently of one another represent hydrogen, $(C_1-C_4)$alkyl, $(C_3-C_6)$alkenyl, $(C_3-C_6)$alkynyl, $(C_3-C_6)$cycloalkyl or

$R^3$ represents methyl, ethyl or trifluoromethyl, $R^4$ represents 2-thienyl or 3-thienyl, $R^5$ represents cyano or thiocarbamoyl, and $R^6$ represents $(C_1-C_6)$alkyl.

4. A method for preventing damage to a plant from phytopathogenic organisms, which comprises applying a compound of claim 1 to the foliage of a plant.

5. A method for preventing damage to a plant from phytopathogenic organisms, which comprises applying a compound of claim 2 to the foliage of a plant.

6. A method for preventing damage to a plant from phytopathogenic organisms, which comprises applying a compound of claim 3 to the foliage of a plant.

7. A method for preventing damage to a plant from phytopathogenic organisms, which comprises applying a compound of claim 1 to the soil in which said plant is growing.

8. A method for preventing damage to a plant from phytopathogenic organisms, which comprises applying a compound of claim 2 to the soil in which said plant is growing.

9. A method for preventing damage to a plant from phytopathogenic organisms, which comprises applying a compound of claim 3 to the soil in which said plant is growing.

10. The method of claim 4, wherein said compound is applied in an amount ranging from 4 to 30 parts per million.

11. The method of claim 7, wherein said compound is applied in an amount ranging from 5 to 9 parts per million.

12. A composition comprising a compound according to claim 1 admixed with an agriculturally acceptable carrier.

13. A composition comprising a compound according to claim 2 admixed with an agriculturally acceptable carrier.

14. A composition comprising a compound according to claim 3 admixed with an agriculturally acceptable carrier.

* * * * *